(12) United States Patent
Igi et al.

(10) Patent No.: US 7,208,634 B2
(45) Date of Patent: Apr. 24, 2007

(54) OXIDATION METHOD OF PRIMARY OR SECONDARY ALCOHOL

(75) Inventors: Kimitaka Igi, Osaka (JP); Makoto Hirata, Osaka (JP); Masafumi Mikami, Osaka (JP)

(73) Assignee: Daiso Co., Ltd., Osaka-Fu (JP)

( * ) Notice: Subject to any disclaimer, the term of this patent is extended or adjusted under 35 U.S.C. 154(b) by 0 days.

(21) Appl. No.: 11/290,474

(22) Filed: Dec. 1, 2005

(65) Prior Publication Data

US 2006/0122434 A1 Jun. 8, 2006

(30) Foreign Application Priority Data

Dec. 3, 2004 (JP) .............................. 2004-350780

(51) Int. Cl.
*C07C 45/29* (2006.01)
(52) U.S. Cl. ...................... 568/322; 568/361; 568/402; 568/431; 568/471
(58) Field of Classification Search .................... None
See application file for complete search history.

(56) References Cited

U.S. PATENT DOCUMENTS

| 5,821,374 | A | 10/1998 | Jenny et al. ................ 549/263 |
| 6,518,419 | B1 * | 2/2003 | Van Der Lugt et al. .... 536/105 |
| 6,540,876 | B1 * | 4/2003 | Cimecioglu et al. ........ 162/177 |
| 2005/0240050 | A1 | 10/2005 | Minamida et al. .......... 560/124 |

FOREIGN PATENT DOCUMENTS

WO 2005/082825 A1 9/2005

OTHER PUBLICATIONS

Einhorn, J. et al., "Efficient and Highly Selective Oxidation of Primary Alcohols to Aldehydes by N-Chlorosuccinimide Mediated by Oxoammonium Salts", *J. Org. Chem.*, vol. 61, pp. 7452 to 7454 (1996).

Anelli, P. C. et al., "Fast and Selective Oxidation of Primary Alcohols to Aldehydes or to Carboxylic Acids and of Secondary Alcohols to Ketones Mediated by Oxoammonium Salts under Two-Phase Conditions", *J. Org. Chem.*, vol. 52, pp. 2559 to 2562 (1987).

Miller, Ross et al., "Iodine as a Chemoselective Reoxidant of TEMPO: Application to the Oxidation of Alcohols to Aldehydes and Ketones", *Organic Letters*, vol. 5, No. 3, pp. 285 to 287 (2003).

De Luca, Lidia et al., "Trichloroisocyanuric/TEMPO Oxidation of Alcohols under Mild Conditions: A Close Investigation", *J. Org. Chem.*, vol. 68, No. 12, pp. 4999 to 5001 (2003).

Liu, Renhua et al., "Highly Efficient Catalytic Aerobic Oxidations of Benzylic Alcohols in Water", *J. Org. Chem.*, vol. 70, No. 2, pp. 729 to 731 (2005).

* cited by examiner

*Primary Examiner*—Sikarl A. Witherspoon
(74) *Attorney, Agent, or Firm*—Wenderoth, Lind & Ponack, L.L.P.

(57) ABSTRACT

A method for preparing an aldehyde or ketone by oxidizing a primary or secondary alcohol in the presence of a nitroxyl radical compound and a co-oxidant in an organic solvent, which process is characterized in using an organic N-bromoamide compound or a combination of N-chlorosuccinimide and a compound having bromide ion as the co-oxidant.

15 Claims, No Drawings

OXIDATION METHOD OF PRIMARY OR SECONDARY ALCOHOL

TECHNICAL FIELD OF THE INVENTION

The present invention relates to a novel method for preparing an aldehyde or ketone by oxidizing a primary or secondary alcohol.

BACKGROUND OF THE INVENTION

The oxidation method of alcohols into aldehydes or ketones is one of the important methods in the organic synthesis. It is known that alcohols can be oxidized with sodium hypochlorite as an oxidizing agent in the presence of catalytic amount of 2,2,6,6-tetramethyl-1-piperidine-1-oxyl radical (Abbreviated as TEMPO hereinafter) (See J. Org. Chem., 1987, 52, p.2529). Furthermore, it is reported that a N-chloro compound such as N-chlorosuccinimide (NCS) or trichloroisocyanuric acid can be used as an oxidizing agent (See U.S. Pat. No. 5,821,374, and J. Org. Chem., 1996, 61, p.7452).

The present inventors have been extensively studied and found that by using a N-bromoamide compound or a combination of NCS and a compound having bromide ion, oxidation of alcohols effectively proceeds in the presence of a TEMPO derivative as catalyst in an organic solvent. Thus the present invention has been completed.

DETAILED DESCRIPTION OF THE INVENTION

The object of the present invention provides a novel method for effectively preparing an aldehyde or ketone by oxidizing a primary or secondary alcohol in an organic solvent.

Namely, the present invention relates to the method for preparing an aldehyde or ketone by oxidizing a primary or secondary alcohol in the presence of a nitroxyl radical compound represented by the following formula (1),

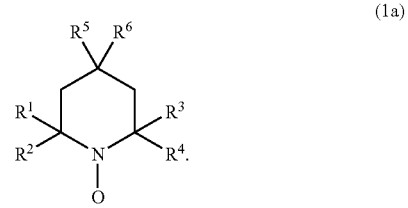

wherein $R^0$ to $R^4$ are the same or different and straight or branched $C_{1-10}$ alkyl group, or two $R^0$s may be combined together with the nitrogen atom in the intramolecule to form a 5 to 7 membered hetero ring, and a co-oxidant in an organic solvent, which process is characterized in using an organic N-bromoamide compound or a combination of N-chlorosuccinimide and a compound having bromide ion as said co-oxidant.

As the present invention is carried out in an organic solvent, troublesome adjustment of pH is not necessary and the degradation of the product hardly occurs. As a brominated compound is used as a co-oxidant, opportunities to use this reaction increase.

Although the catalyst used in the present invention is a catalyst represented by the above formula (1), it may include such a compound wherein at least one of $R^0$ to $R^4$ represents $C_{1-6}$ alkyl group substituted by $C_{1-6}$ alkoxy group in the formula (1), as long as it does not deviate from the aim of the present invention.

The catalyst of the formula (1) is known and prepared by the methods described in European Patent 574666 and 574667, etc.

In the catalyst (1) is preferable a compound of the following formula (1a),

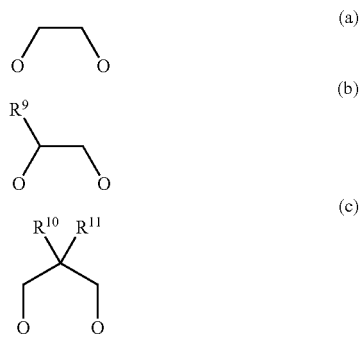

wherein $R^1$ to $R^4$ are the same as defined above, $R^5$ and $R^6$ are both hydrogen atom or both $C_{1-6}$ alkoxy group, or one of $R^5$ and $R^6$ is hydrogen atom and the other is hydroxy group, $C_{1-6}$ alkoxy group, acyloxy group, or acylamino group, or $R^5$ and $R^6$ taken together may form any one of ketal groups of the formulas (a) to (c),

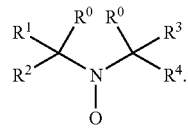

wherein $R^9$ is $C_{1-6}$ alkyl, and $R^{10}$ and $R^{11}$ are both hydrogen atom or the same or different and are $C_{1-6}$ alkyl group.

The compound (1a) wherein $R^1$ to $R^4$ are all methyl group, and $R^5$ and $R^6$ are both hydrogen atom, or one of $R^5$ and $R^6$ is hydrogen atom and the other is hydroxy group, methoxy group, acetoxy group, benzoyloxy group or acetamide group is especially preferable.

The amount of the catalyst (1) or (1a) is preferably 0.01 to 30 mole % against a substrate, an alcohol, especially preferably 0.05 to 5 mole %.

The preferable organic N-bromoamide compound used as a co-oxidant in this invention includes N-bromoactetamide (NBA), N-bromosuccinimide (NBS), tribromoisocyanuric acid, dibromo dimethyl hydantoin, N-bromophthalimide and so on. NBA and NBS among them are especially preferable.

When a combination of N-chlorosuccinimide and a compound having bromide ion is used as a co-oxidant, an alkali metal bromide such as sodium bromide or potassium bromide, and a quaternary ammonium bromide such as tetrabutylammonium bromide or benzyltrimethylammonium bromide are preferably used as a compound having bromide ion (a source of said bromide ion).

When an organic N-bromoamide compound is used as a co-oxidant, the amount of the organic N-bromoamide compound is 1.05 to 2 molar equivalents against a substrate, an alcohol and more preferably 1.1 to 1.5 molar equivalents.

On the other hand, when a combination of N-chlorosuccinimide and a compound having bromide ion is used as a co-oxidant, the amount of N-chlorosuccinimide is preferably 1.05 to 2 molar equivalents against a substrate, an alcohol and more preferably 1.1 to 1.5 molar equivalents. The amount of the compound having bromide ion is preferably 1 to 100 mole % against a substrate, an alcohol and more preferably 5 to 20 mole %.

The alcohol used as a substrate in the present invention is not limited as long as it has an alcoholic primary or secondary hydroxy group, for example, a straight or branched primary or secondary alkyl alcohol such as 1-octanol, 1-nonanol or 2-octanol, a cycloalkyl alcohol such as cyclohexanol or cyclobutanol, or an alcohol having substituted or unsubstituted aralkyl group such as phenethyl alcohol, benzyl alcohol or p-methoxybenzyl alcohol. Furthermore, glycerol acetonide is also preferably used.

It is not necessary to use water in the present invention. In order to adjust the viscosity the suitable organic solvent may be used, if necessary, for example an ether-solvent such as tetrahydrofuran (THF), diethyl ether, 1,2-diethoxyethane or methyl t-butyl ether (MTBE), an ester-solvent such as ethyl acetate or butyl acetate, an aromatic hydrocarbon-solvent such as benzene or toluene, a hydrocarbon-solvent such as hexane or heptane, a ketone-solvent such as acetone or methylethylketone, a halogeno compound-solvent such as dichloromethane or 1,2-dichloroethane, or a tertiary alcohol such as t-butanol or t-amyl alcohol. The ester-solvent, the ketone-solvent and the halogeno compound-solvent are preferably used.

The reaction temperature is not critical, and preferably, is −50 to 100° C. and more preferably −15 to 30° C.

In order to neutralize hydrogen bromide occurring in the oxidation reaction of the present invention, a base may be used such as preferably an inorganic base such as sodium acetate, sodium hydrogencarbonate, potassium carbonate, sodium phosphate or potassium hydrogenphosphate, or an organic base such as triethylamine, diisopropylethylamine or pyridine. When the aldehyde produced is unstable, the aldehyde may be converted into a stable compound by reacting it with a suitable compound.

When an optically active alcohol as a substrate is used, the remarkable racemization does not occur by the oxidation reaction of the present invention and the object aldehyde compound with the optical configuration is obtainable.

EXAMPLE

The present invention is explained by the following examples, but the scope of the present invention should not be limited by them. In each example, the product produced was confirmed by showing the same retention time as the standard by gas chromatography.

Example 1

Manufacture of 1-octanal

1-Octanol (2.0 g, 15.4 mmol), sodium hydrogencarbonate (1.6 g, 18.5 mmol), TEMPO (24 mg, 0.15 mmol) and dichloromethane (15 ml) were put in a 50-ml egg plant type flask. The suspension was cooled to less than 10° C. in an ice bath, and thereto was added NBS (3.0 g, 16.9 mmol) divided in three portions. The insoluble materials were filtered off and the filtrate was washed with 5% aqueous sodium bicarbonate solution. The crude product was purified by distillation to give 1-octanal (1.74 g, yield 88%).

Example 2

Manufacture of 1-Octanal

1-Octanol (2.0 g, 15.4 mmol), sodium acetate (1.8 g, 21.6 mmol), 4-hydroxy TEMPO (53 mg, 0.31 mmol) and dichloromethane (15 ml) were put in a 50-ml egg plant type flask. The suspension was cooled to less than 10° C. in an ice bath, and thereto was added NBA (2.5 g, 18.5 mmol)divided in two portions. The insoluble materials were filtered off and the filtrate was washed with 5% aqueous sodium bicarbonate solution. The crude product was purified by distillation to give 1-octanal (1.78 g, yield 90%).

Example 3

Manufacture of 1-octanal

1-Octanol (2.0 g, 15.4 mmol), sodium hydrogencarbonate (1.6 g, 18.5 mmol), 4-methoxy TEMPO (29 mg, 0.15 mmol), sodium bromide (0.16 g, 1.54 mmol) and 1,2-dichloroethane (15 ml) were put in a 50-ml egg plant type flask. The suspension was cooled to less than 10° C. in an ice bath and thereto was added NCS (2.3 g, 16.9 mmol) divided in two portions. The insoluble materials were filtered off and the filtrate was washed with 5% aqueous sodium bicarbonate solution. The crude product was purified by distillation to give 1-octanal (1.67 g, yield 85%).

Example 4

Manufacture of 1-hexanal

1-Hexanol (2.0 g, 19.6 mmol), sodium carbonate (1.2 g, 11.8 mmol), 4-acetoamino TEMPO (42 mg, 0.20 mmol) and dichloromethane (15 ml) were put in a 50-ml egg plant type flask. The suspension was cooled to less than in an ice bath and thereto was added NBS (3.8 g, 21.6 mmol) divided in four portions. The insoluble materials were filtered off and the filtrate was washed with 5% aqueous sodium bicarbonate solution. The crude product was purified by distillation to give 1-hexanal (1.77 g, yield 90%).

Example 5

Manufacture of phenylacetaldehyde

β-Phenethylalcohol (2.0 g, 16.4 mmol), sodium acetate (2.0 g, 24.6 mmol), TEMPO (26 mg, 0.16 mmol) and ethyl acetate (15 ml) were put in a 50-ml egg plant type flask. The suspension was cooled to less than 10° C. in an ice bath, and thereto was added NBS (3.2 g, 18.0 mmol) divided in two portions. The insoluble materials were filtered off and the filtrate was washed with 5% aqueous sodium bicarbonate solution. The crude product was purified by distillation to give phenethylacetaldehyde (1.67 g, yield 85%).

Example 6

Manufacture of 2-octanone

2-Octanol (2.0 g, 15.4 mmol), sodium hydrogencarbonate (1.6 g, 18.5 mmol), TEMPO (24 mg, 0.15 mmol) and 1,2-dichloroethane (15 ml) were put in a 50-ml egg plant type flask. The suspension was cooled to less than 10° C. in an ice water bath, and thereto was added NBS (3.0 g, 16.9 mmol) divided in two portions. The insoluble materials were filtered off and the filtrate was washed with 5% aqueous sodium bicarbonate solution. The crude product was purified by distillation to give 2-octanone (1.88 g, yield 95%).

Example 7

Manufacture of cyclohexanone

Cyclohexanol (2.0 g, 20 mmol), sodium carbonate (1.3 g, 12 mmol), 4-acetoaminoTEMPO (43 mg, 0.2 mmol) and THF (15 ml) were put in a 50-ml egg plant type flask. To the suspension was added NBS (3.9 g, 22 mmol) divided in two portions. The insoluble materials were filtered off and the filtrate was washed with 5% aqueous sodium bicarbonate solution. The crude product was purified by distillation to give cyclohexanone (1.73 g, yield 88%).

Example 8

Manufacture of benzaldehyde

Benzyl alcohol (2.0 g, 18.5 mmol), potassium carbonate (1.5 g, 11.1 mmol), 4-hydroxy TEMPO (31 mg, 0.19 mmol), tetrabutylammonium bromide (0.5 g, 1.9 mmol) and MTBE (15 ml) were put in a 50-ml egg plant type flask. The suspension was cooled to less 10° C. in an ice bath and thereto was added NCS (2.7 g, 20.4 mmol) divided in three portions. The insoluble materials were filtered off and the filtrate was washed with 5% aqueous sodium bicarbonate solution. The crude product was purified by distillation to give benzaldehyde (1.77 g, yield 90%).

Example 9

Manufacture of p-anisaldehyde p-Methoxybenzyl alcohol (2.0 g, 14.5 mmol), sodium carbonate (0.9 g, 8.7 mmol), TEMPO (23 mg, 0.15 mmol), benzyltrimethylammonium bromide (0.3 g, 1.5 mmol) and dichloromethane (15 ml) were put in a 50-ml egg plant type flask. The suspension was cooled to less than 10° C. in an ice bath and thereto was added NCS (2.1 g, 16 mmol) divided in two portions. The insoluble materials were filtered off and the filtrate was washed with 5% aqueous sodium bicarbonate solution. The crude product was purified by distillation to give p-anisaldehyde (1.62 g, yield 82%).

Example 10

Manufacture of (R)-3-(2,2-dimethyl-1,3-dioxolan-4-yl)-2-propenoic acid methyl ester (R)-Glycerol acetonide (5.0 g, 37.8 mmol), sodium hydrogencarbonate (4.8 g, 56.7 mmol), 4-acetoxy TEMPO (41 mg, 0.19 mmol) and THF (50 ml) were put in a 200-ml three neck-flask. The suspension was cooled to less than 10° C., and thereto was added NBS (8.1 g, 45.4 mmol) divided in three portions. The insoluble materials are removed by filtration and the filtrate was cooled to 0° C. Thereto was added methyl(triphenylphosphoranylidene)acetate (15.1 g, 45.4 mmol) and the mixture was stirred at 0° C. for 16 hours. To the reaction mixture was added hexane (100 ml) and the insoluble materials were filtered off and the filtrate was concentrated. The crude product was purified by silica gel chromatography to give the object ester (trans form/cis form=29/71) (5.3 g, yield 75%).

The present invention relates to a method for preparing an aldehyde or a ketone by oxidizing a primary or secondary alcohol. The compound thus prepared is utilized in the organic synthesis-industry.

What is claimed is:

1. A process for preparing an aldehyde or ketone by oxidizing a primary or secondary alcohol in the presence of a nitroxyl radical compound represented by the following formula (1),

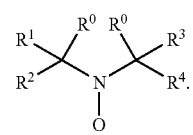

(1)

wherein $R^0$ to $R^4$ are the same or different and straight or branched $C_{1-10}$ alkyl group, or two $R^0$s may be combined together with the nitrogen atom to form a 5 to 7 membered hetero ring, and a co-oxidant in an organic solvent, which process comprises using an organic N-bromoamide compound or a combination of N-chlorosuccinimide and a compound having bromide ion as said co-oxidant.

2. The process of claim 1 wherein the nitroxyl radical compound is a compound of the following formula (1a),

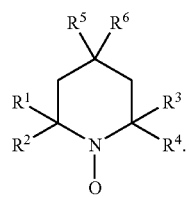

(1a)

wherein $R^1$ to $R^4$ are the same as defined above, $R^5$ and $R^6$ are both hydrogen atom or both $C_{1-6}$ alkoxy group, or one of $R^5$ and $R^6$ is hydrogen atom and the other is hydroxy group, $C_{1-6}$ alkoxy group, acyloxy group or acylamino group, or $R^5$ and $R^6$ taken together may form any one of ketal groups of the formulas (a) to (c),

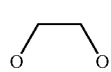

(a)

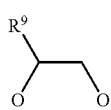

(b)

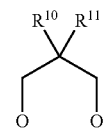

(c)

wherein $R^9$ is $C_{1-6}$ alkyl, and $R^{10}$ and $R^{11}$ are both hydrogen atom or the same or different and are $C_{1-6}$ alkyl group.

3. The process of claim 2 wherein the nitroxyl radical compound is a compound of the formula (1a) wherein $R^1$ to $R^4$ are all methyl groups, and $R^5$ and $R^6$ are both hydrogen atom, or one of $R^5$ and $R^6$ is hydrogen atom and the other is hydroxy group, methoxy group, acetoxy group, benzoyloxy group or acetamide group.

4. The process of any one of claims 1 to 3 wherein the co-oxidant is an organic N-bromoamide compound.

5. The process of claim 4 wherein the organic N-bromoamide compound is N-bromosuccinimide or N-bromoacetamide.

6. The process of any one of claims 1 to 3 wherein the co-oxidant is a combination of N-chlorosuccinimide and a compound having bromide ion.

7. The process of claim 6 wherein the compound having bromide ion is an alkali metal bromide or a quaternary ammonium bromide.

8. The process of claim 6 wherein the compound having bromide ion is sodium bromide or potassium bromide.

9. The process of any one of claims 1 to 3 wherein the co-oxidant is N-bromoacetamide, N-bromosuccinimide, tribromoisocyanuric acid, dibromo dimethyl hydantoin, N-bromophthalimide or a combination of N-chlorosuccinimide and a compound having bromide ion.

10. The process according to claim 1, which process consists essentially of using N-bromoacetamide, N-bromosuccinimide, tribromoisocyanuric acid, dibromo dimethyl hydantoin, N-bromophthalimide or a combination of N-chlorosuccinimide and a compound having bromide ion as said co-oxidant.

11. The process according to claim 9, which process consists essentially of using N-bromoacetamide, N-bromosuccinimide, tribromoisocyanuric acid, dibromo dimethyl hydantoin, N-bromophthalimide or a combination of N-chlorosuccinimide and a compound having bromide ion as said co-oxidant.

12. The process according to claim 10 wherein the co-oxidant is N-bromosuccinimide or N-bromoacetamide.

13. The process according to claim 10 wherein the co-oxidant is a combination of N-chlorosuccinimide and a compound having bromide ion.

14. The process according to claim 11 wherein the co-oxidant is N-bromosuccinimide or N-bromoacetamide.

15. The process according to claim 11 wherein the co-oxidant is a combination of N-chlorosuccinimide and a compound having bromide ion.

* * * * *